United States Patent [19]

Matz et al.

[11] Patent Number: 5,532,413
[45] Date of Patent: Jul. 2, 1996

[54] STORAGE STABLE BIOCIDE COMPOSITION AND PROCESS FOR MAKING THE SAME

[75] Inventors: Gary F. Matz, Rosslyn Farms; Paul F. Richardson, Pittsburgh, both of Pa.

[73] Assignee: Calgon Corporation, Pittsburgh, Pa.

[21] Appl. No.: 369,612

[22] Filed: Jan. 6, 1995

[51] Int. Cl.$^6$ ............................................. C07C 277/02
[52] U.S. Cl. ............................................. 564/240; 564/232
[58] Field of Search ................................ 564/232, 240; 514/634

[56] References Cited

U.S. PATENT DOCUMENTS

| | | | |
|---|---|---|---|
| 2,867,562 | 1/1959 | Lamb | 167/22 |
| 2,906,595 | 9/1959 | Pelcak et al. | 21/2.7 |
| 3,116,326 | 12/1963 | Lamb | 260/56 |
| 3,142,615 | 7/1965 | Chehner | 167/22 |
| 3,143,459 | 8/1964 | Marks et al. | 167/42 |
| 3,264,172 | 8/1966 | Regutti | 162/161 |
| 3,628,941 | 12/1971 | Marks | 71/67 |

Primary Examiner—Peter O'Sullivan
Attorney, Agent, or Firm—Craig G. Cochenour

[57] ABSTRACT

An antimicrobial composition comprising the formula

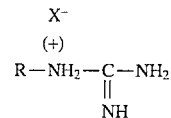

wherein R is an alkyl group having a distribution of carbon atoms from about eight to eighteen carbon atoms and wherein from about 40 to 60 weight % of the alkyl group having about twelve carbon atoms and wherein X is hydrogen or a halide is disclosed. The antimicrobial composition is storage stable below about 5° C. and, further, preferably, also has a flash point above about 38° C. A process for making this antimicrobial composition is disclosed resulting in an antimicrobial composition comprising from about 25 to 35 weight % of the alkyl guanidine halide salt of the above formula, from about 10 to 60 weight % of a solvent and from about 10 to 65 weight % water.

6 Claims, No Drawings

STORAGE STABLE BIOCIDE COMPOSITION AND PROCESS FOR MAKING THE SAME

BACKGROUND OF THE INVENTION

1. Field of the Invention

The present invention is concerned with an antimicrobial composition which is useful for inhibiting microbial growth wherever such microbial growth is undesirable, e.g. aqueous systems found in a variety of industrial applications, such as, for example, papermaking and cooling water applications. More particularly, the present invention is concerned with an alkyl guanidine composition and salts thereof that are storage stable at temperatures below 5° C. A process for making the same is also disclosed.

2. Description of the Background Art

As used herein, the phrases "biocide", "antimicrobial", and "inhibiting microbial growth" describe the killing of, as well as the inhibition of or control of, biological growth including, but not limited to, bacteria, yeasts, fungi, and algae. A number of important industries have experienced serious adverse effects from the activity of such biological growth on the raw materials which they employ, on various aspects of their manufacturing activities, or on the finished products which they produce. Such industries include, for example, but are not limited to, the paint, wood, textile, cosmetic, leather, tobacco, fur, rope, paper, pulp, plastics, fuel, oil, rubber and machine industries.

The present invention provides an improved biocide compound, namely an alkyl guanidine composition and salts thereof, which exhibits superior storage stability at low temperatures as compared to alkyl guanidine hydrochloride compounds known in the art. It will be appreciated by those skilled in the art that mineral acid or monocarboxylic acid salts of alkyl guanidines are known for their antimicrobial activity such as disclosed, for example, in U.S. Pat. Nos. 2,867,562, 2,906,595, 3,116,326, 3,142,615, 3,143,459, 3,264,172 and 3,628,941. The acid salts of dodecylguanidine are the best known and widely used compounds of the class.

Dodecylguanidine hydrochloride (DGH) is an alkyl guanidine hydrochloride wherein the alkyl group has a twelve carbon chain. Typically, DGH is synthesized by reacting very pure lauryl amine, i.e. $C_{12}$>98%, with hydrogen cyanamide in hydrochloric acid, water, and isopropyl alcohol (IPA). The DGH produced by this method, however, has poor storage stability. Storage stability of alkyl guanidine antimicrobial compositions has been an ongoing problem, particularly during cold weather. At low temperatures such as, for example, below 5° C. and more particularly below 0° C., and/or during temperature freezing and thawing situations, DGH prepared by this known method tends to precipitate or wax out of solution which presents a severe handling problem.

Another problem associated with DGH as it is currently manufactured is its relatively low flash point, for example less than 38° C. As with any composition containing significant levels of IPA, the potential flammability of DGH is unacceptably high for use in many industrial applications. Attempts to alter the amount of IPA used in DGH production have met with only limited success. For example, DGH formulations with less IPA have a higher flash point and are therefore safer to use, but also have a lower percentage of active alkyl guanidine. DGH formulations with higher amounts of active alkyl guanidine have more IPA and therefore a lower flash point which makes them more flammable. This problem makes the use of DGH prohibitive for many industries which require the use of biocides.

In spite of this background material, there remains a very real and substantial need for an alkyl guanidine antimicrobial composition and process for making the same having improved storage stability at temperatures below 5° C. and a flash point above 38° C. for providing safer handling than other alkyl guanidine salts known in the art.

SUMMARY OF THE INVENTION

The present invention has met the above described needs. The present invention provides an antimicrobial composition comprising the formula:

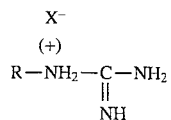

wherein R is an alkyl group having a distribution of carbon atoms from about eight to eighteen carbon atoms, and wherein from about 40 weight % to 60 weight % of the alkyl group having about twelve carbon atoms, and wherein X is hydrogen or a halide selected from the group consisting of chloride, bromide, fluoride and iodide. The composition of the present invention has storage stability at temperatures below about 5° C. that is superior to results of others previously achieved. In a preferred embodiment of the present invention, the antimicrobial composition, as described herein, is storage stable at temperatures below about 5° C. and has a flash point temperature above about 38° C.

Another embodiment of the present invention provides a process in which the antimicrobial composition, as described herein, having unexpectedly improved properties is made comprising mixing a technical grade alkyl amine, wherein the alkyl group has a carbon chain length distribution from about eight to eighteen carbon atoms such that from about 40 to 60 weight % of the alkyl group has a twelve carbon chain, with a solvent in a reactor, adding hydrochloric acid to the reactor, adding hydrogen cyanamide to the reactor at a rate sufficient for maintaining the temperature of the above-described mixture from about 75° C. to 95° C., holding this mixture at a temperature from about 75° C. to 95° C. for about 2 hours, cooling this mixture to below about 30° C., adding a sufficient amount of solvent or water to dilute the above-described mixture to the desired concentration, and adjusting the pH of the above-described mixture to less than about 1.0 and preferably from about 0.4 to 0.6. Preferably, this process includes employing dipropylene glycol as the solvent for preparing an antimicrobial composition of the present invention that is storage stable at temperatures below 5° C. and that has a flash point at a temperature above about 38° C.

In another embodiment of the invention, an antimicrobial composition is provided that is storage stable at temperatures below 5° C. comprising from about 25 to 35 weight % of an alkyl guanidine of the formula of the present invention described herein, from about 10 to 60 weight % of a solvent, and about 10 to 65 weight % water.

DETAILED DESCRIPTION OF THE INVENTION

The present invention is directed to a storage stable alkyl guanidine composition and salts thereof and a process of making the same for use as a biocide in water treatment applications, particularly, for example, in paper making processes and cooling water applications. As noted herein, the novelty of the present invention derives from the improved storage stability of the alkyl guanidine compositions at temperatures below 5° C. A further unexpected advantage of the composition of the present invention is that the alkyl guanidine composition, when synthesized using the process of the instant invention employing dipropylene glycol as a solvent, has a flash point above about 38° C., therefore allowing for safer handling.

The present invention provides an antimicrobial composition comprising an alkyl guanidine (AGH) having the following formula:

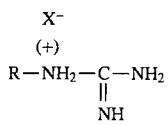

wherein R is an alkyl group having from about eight to eighteen carbon atoms, and preferably wherein R is an alkyl group having a distribution of carbon chain lengths ranging from about $C_8$ to $C_{18}$ and wherein X is hydrogen or is a halide selected from the group consisting of fluoride, chloride, bromide, and iodide. It will be appreciated by those skilled in the art that naturally occurring coco amine has a distribution of carbon chain lengths ranging from about $C_8$ to $C_{18}$. Most preferably, the composition of the instant invention is derived from a coco amine wherein about 40 to 60 weight % of the alkyl group of the coco amine has a carbon chain of about twelve carbon atoms. It is important to note that the applicant has unexpectedly discovered that the antimicrobial composition as described herein is storage stable at temperatures below about 5° C. and has a flash point above about 38° C.

Another embodiment of the present invention provides an antimicrobial composition storage stable at temperatures below 5° C. comprising from about 25 to 35 weight % of an alkyl guanidine of the formula

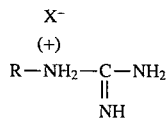

wherein R is an alkyl group having a distribution of carbon chain length ranging from about eight to eighteen carbon atoms, wherein from about 40 weight % to 60 weight % of the alkyl group has a carbon chain of about twelve carbon atoms, and wherein X is hydrogen or a halide selected from the group consisting of chloride, bromide, fluoride and iodide; from about 10 weight % to 60 weight % of a solvent; and from about 10 to 65 weight % water. The solvent is selected from the group consisting of an alcohol having a carbon chain length of at least three carbon atoms and a glycol. Preferably, this antimicrobial composition, as described herein, includes from about 1 to 5 weight % unreacted starting materials selected from the group consisting of coco amine and hydrogen cyanamide. Most preferably the solvent of the antimicrobial composition is dipropylene glycol with the resulting antimicrobial composition having improved storage stability at temperatures below about 5° C. and a flash point at a temperature above about 38° C.

Relative to the process of the instant invention, the applicant has discovered that the level of purity of the alkyl amine starting material is directly related to the storage stability of the final composition. Historically, a lauryl amine having a high purity, such as, for example, $C_{12}>98$ weight %, was used in the manufacture of alkyl guanidine hydrochlorides, specifically dodecylguanidine hydrochloride (DGH). In contrast, the process of the present invention comprises employing a technical grade alkyl amine such that from about 40 to 60 weight % of the alkyl group has a twelve carbon atom chain. Amine KKD, a coco amine which meets these parameters and which is commercially available from the Berol Nobel Company, is one such technical grade lauryl amine. It is important in the process of the instant invention that the remaining 40 to 60 weight % of the alkyl groups in the technical grade alkyl amine have a distribution of carbon chain lengths of between eight and eighteen carbon atoms.

Because of the alkyl amine starting material employed in the process of the present invention as described herein, the resulting alkyl guanidine composition will similarly have a distribution of alkyl groups having between eight and eighteen carbons with from about 40 to 60 weight % of the alkyl groups having 12 carbon atoms. The unexpected finding of the process of the present invention is that the broad distribution of carbon chain lengths employed results in an antimicrobial composition of the instant invention having storage stability at lower temperatures than previously achieved by others.

The antimicrobial composition of the present invention is produced by a process comprising reacting the technical grade alkyl amine such as, for example, lauryl amine, with a solvent in a reactor. As hereinbefore stated, the technical grade alkyl amine includes wherein the alkyl group has a carbon chain length distribution from about eight to eighteen carbon atoms and such that from about 40 to 60 weight % of the alkyl group has a twelve carbon chain. The solvent is an alcohol having a carbon chain length having at least about three (3) carbon atoms, and includes, such as for example, isopropyl alcohol, or a glycol such as, for example, ethylene glycol, propylene glycol and dipropylene glycol. The process of the instant invention further includes adding hydrochloric acid (35% W/W) and hydrogen cyanamide solution (50% W/W) sequentially to the reactor, heating the mixture of the alkyl amine, solvent, hydrochloric acid and hydrogen cyanamide to a temperature ranging from about 75° to 95° C. for about four hours. The precise temperature is dependent upon the boiling point of the solvent employed, as will be understood by those skilled in the art. The process further includes cooling the mixture to below about 30° C., and preferably to about 22° C., adding additional solvent and/or water, and adjusting the pH of the mixture to less than about 1, and preferably from about 0.4 to 0.6, with additional hydrochloric acid. This process yields an antimicrobial composition in which the AGH active ingredient as described herein comprises from about 25 to 35 weight % of the total product, and wherein the solvent is from about 10 to 60 weight % of the final product and wherein water is about 10 to 65 weight % of the final product. The resulting solution is generally a clear, light amber color and is free of foreign matter.

In another embodiment of the present invention, a process is provided for making the storage stable biocide composition of the present invention, as described herein, including employing a solvent selected upon the importance of the desired flash point of the resulting biocide composition. To obtain a biocide composition having a lower flash point (i.e., below 38° C.), isopropyl alcohol is the preferred solvent. To obtain a composition with a higher flash point (i.e., above 38° C.), the preferred solvent is dipropylene glycol. Thus, it will be appreciated that the applicant has discovered that dipropylene glycol is the preferred solvent to be employed with the alkyl amine starting material of the process of the present invention to obtain an antimicrobial composition of the present invention having both a high flash point and storage stability below 5° C. Dipropylene glycol is commercially available from AC West Va. Polyal Co., Van Water & Rogers, Kodak or Dow Chemical.

The antimicrobial composition of the present invention is used, for example, in liquid concentrate form. Typical use levels indicate that the antimicrobial composition of the instant invention is effective in the range of 0.0025 to 0.1% (25 to 1,000 parts per million (ppm)). The exact amount of any given formulation of the composition of the instant invention employed will vary depending on the storage time and storage temperature desired and the aqueous system being treated.

Applications of the alkyl guanidine composition and salts thereof of the present invention include the prevention of biological growth, for example, in paper processes, particularly alkaline paper making processes, cooling water, and other processes in which water treatment is necessary. The antimicrobial composition of the instant invention is also particularly effective against growth of sulfate reducing bacteria. Other applications of the antimicrobial composition of the present invention include, such as for example, but not limited to, use as a manufacturing and end-use product for reduction of growth of algae, bacteria, and mollusks in commercial and industrial cooling water systems and sewage lagoons; control of microorganisms such as bacteria, fungi, and yeasts which cause deterioration of paper and paperboard products; control of slime-forming bacteria and fungi in air washer systems and brewery pasteurizers; control of bacteria and fungi in pulp and paper mill systems; control of biological growth in auxiliary and standby cooling water systems; control of algae, bacteria, and fungi in oil recovery drilling fluids and oil field water systems; and use as a bacteriostat in disposable diapers. Further, the antimicrobial composition of the present invention as disclosed herein effectively inhibits the growth of microorganisms in aqueous systems such as, for example, paste and adhesive systems, polymer and latex emulsion systems, pigmented slurries and coating slurries, titanium dioxide, and calcium carbonate systems.

The following examples are set forth to illustrate the invention in greater detail. These examples are not intended to limit the scope of the present invention in any way.

EXAMPLE I

Alkyl Guanidine Hydrochloride (AGH) Prepared By the Preferred Embodiment

The preferred embodiment of the process of the present invention was carried out according to the following example, with Table 1 representing the amount of each starting material used for a yield of 999 grams of product.

TABLE 1

| Item # | Name | Amount of raw material per 999 grams of product |
| --- | --- | --- |
| 1 | Dipropylene Glycol | 600 grams |
| 2 | Amine KKD (obtained from Berol Nobel) | 180 grams |
| 3 | 5% Hydrochloric Acid | 107 grams |
| 4 | 50% Hydrogen Cyanamide | 112 grams |

One hundred and ten grams Dipropylene Glycol (DPG) and 180 grams Amine KKD were added to a glass reactor. Eighty-five grams concentrated hydrochloric acid (HCl) were added to the reactor over about a 20 minute time period, allowing the heat of the neutralization to warm the reactor from about 22° to 95° C. Over about a four hour period, 112 grams of hydrogen cyanamide solution were added to the reactor, while maintaining the temperature from about 75° C. to 95° C. The mixture was held at this temperature for about 2 hours (i.e., hold period). After the hold period, the reactor was cooled to ambient temperature (i.e., about 22° C.); during cooling, 490 grams DPG were added to the reactor over a 30 minute period. Twenty two grams of concentrated HCl were added to the reactor to adjust the pH of the mixture to about 0.4 to 0.6; the mixture was cooled to ambient temperature and discharged. The resulting product had about 25 weight % AGH, about 60 weight % dipropylene glycol, about 12.5 weight % water, and about 2.5 weight percent of unreacted starting material including the alkyl amine Amine KKD and hydrogen cyanamide.

EXAMPLE II

Alkyl Guanidine Hydrochloride Prepared Using Isopropyl Alcohol

Another embodiment of carrying out the process of the present invention is provided using Amine KKD and isopropanol as the solvent according to the following example. Table 2 lists the amounts of each starting material used for a yield of 1000 pounds of product.

TABLE 2

| Item | Amount of raw material per 1000 pounds of product |
| --- | --- |
| Isopropyl Alcohol | 156.7 |
| Amine KKD | 256.4 |
| 35% Hydrochloric Acid | 159.1 |
| 50% Hydrogen Cyanamide | 145.3 |
| Tap Water | 282.5 |

Approximately one hundred fifty six pounds of isopropyl alcohol (IPA) and about 256 pounds of Amine KKD were added to a glass reactor. About 131 pounds concentrated hydrochloric acid (HCl) were slowly added to the reactor, allowing the heat of the neutralization to warm the reactor from about 80° C. to 85° C. at which point the mixture began to reflux. Approximately 145 pounds of hydrogen cyanamide solution were added to the reactor at the rate of 0.64 pounds/minute. Upon addition of all of the hydrogen cyanamide, the mixture was refluxed for at least 3 hours. After refluxing, the reactor was cooled to ambient temperature; during cooling, about 282 pounds of tap water were added to the reactor. About twenty seven pounds of concentrated HCl were added to the reactor to adjust the pH of the mixture to about 0.4 to 0.6; the mixture was cooled to ambient temperature and discharged. The resulting product had about 25 weight % AGH, about 15.5 weight % IPA and about 59.5 weight % water.

EXAMPLE III

Low Temperature Stability of AGH

AGH sample compositions prepared with various grades and types of alkyl amines were tested to determine which alkyl amine starting material yields the most storage stable product. The AGH sample compositions tested included dodecylguanidine hydrochloride $C_{12}$>98%, two different AGH composition samples of distilled coco amine (i.e., Amine KKD lot number 1990-10-02 and Amine KKD lot number DE 91105) obtained from Berol Nobel, and a high purity octyl amine (Amine 8D greater than 98% $C_8$), also obtained from Berol Nobel. The distribution of carbon chains in the AGH composition of each of these samples is reproduced in Table 3. Each of the AGH compositions was prepared according to the procedures outlined in Example II for production of AGH utilizing IPA as the solvent. Storage data was then collected on these AGH compositions. Storage data was collected over a two week period in a 4° C. refrigerator, and in addition, freeze-thaw data was collected by placing samples in a freezer (−10° C.) overnight for about 16 hours, removing them in the morning, and thawing them at room temperature. This freeze-thaw cycle was repeated three times. In all cases, samples were observed for signs of precipitation and freezing. The cold storage results are reported in Table 3.

TABLE 3

| Alkyl Amine raw material Sample | Carbon Chain Length[1] | | | | | | | Cold Storage Stable[2] |
|---|---|---|---|---|---|---|---|---|
| | C6 | C8 | C10 | C12 | C14 | C16 | C18 | |
| dodecyl- amine | | | | 100 | | | | No |
| Amine KKD (1990- 10-02) | | 2 | 4 | 55 | 22 | 11 | 6 | Yes |
| Amine KKD (DE 91105) | | 2 | 4 | 49 | 19 | 13 | 14 | Yes |
| Amine 8D | 1 | 98 | 1 | No | | | | |

[1] in weight %
[2] at or below about 5° C.

The results set forth in Table 3 show that employing greater than 98% pure amine starting material (i.e., dodecylamine and Amine 8D) resulted in a composition that was not cold storage stable. In contrast, the compositions of the present invention having a broad distribution of alkyl carbon chain lengths, more specifically from about 40 to 60 weight % $C_{12}$, such as those in Amine KKD, resulted in a product with superior storage stability at temperatures at or below 5° C.

EXAMPLE IV

Efficacy of Reformulated AGH and Comparison with Efficacy of DGH

The following example shows the biocidal efficacy in a microtiter test of the antimicrobial composition of the present invention and an antimicrobial composition containing dodecylguanidine hydrochloride, $C_{12}$>98% that is currently commercially available from Calgon Corporation, Pittsburgh, Pa., against a variety of bacteria and fungi. A sample of the antimicrobial composition of the instant invention was prepared by using the method described in Example I utilizing DPG as the solvent. The antimicrobial composition of the instant invention and the dodecylguanidine composition prepared by methods currently known by those skilled in the art were tested against a variety of bacteria, mold, and yeast on an equal ACTIVE basis.

First, the Minimal Inhibitory Concentration (MIC) was determined. The MIC is the least amount of biocide that results in no evidence of growth, with growth being defined as turbidity or a "button" of cells at the bottom of the well. To make this determination, concentrations ranging from about 3.9 ppm to 2000 ppm active dodecylguanidine hydrochloride wherein the alkyl group has a twelve carbon chain ($C_{12}$>98%) known in the art and the antimicrobial composition of the instant invention prepared by the process set forth under Example I herein, were each separately tested in two-fold dilutions in a 96-well microwell plate against a variety of bacteria, mold and yeast on an equal active basis. A list of the organisms tested is found in Tables 4 and 5. The microtiter system employed in determining the biostatic properties of compounds against a variety of organisms is well known by those skilled in the art. Bacterial plates were incubated at 37° C. for about 24 hours at pH 8.0 then read using an Automatic Microplate Reader, a technique known by those skilled in the art. Yeast and mold plates were incubated at 30° C. for about 72 hours, pH 8.0 and then read using a Reading Mirror, a technique known by those skilled in the art. The MIC for each organism tested is shown in Tables 4 and 5. Each MIC value shown is an average concentration of two wells.

The Minimal Biocidal Concentration (MBC) was then determined. The MBC is the concentration of biocide which results in no evidence of growth after subculturing at various times. The subcultures of the bacterial, yeast, and mold plates were subjected to MBC testing made after two, four, and twenty four hours respectively, as shown in Tables 4 and 5. In most cases, the MBC decreased as the time of subculturing increased. The test results for the dodecylguanidine hydrochloride wherein the alkyl group has a twelve carbon chain C>98% are set forth in Table 4 and the test results for the antimicrobial composition of the present invention are set forth in Table 5.

TABLE 4

| | | (dodecylguanidine hydrochloride, $C_{12}$>98%) | | | | |
|---|---|---|---|---|---|---|
| ORGANISM | TYPE | CULTURE MEDIUM | MIC | 2 HR MBC | 4 HR MBC | 24 HR MBC |
| *Pseudomonas aeruginosa* ATCC 10145 | B | TGE | 62.5* | 312.5 | 93.8 | 125 |
| *Klebsiella pneumoniae* ATCC 4352 | B | TGE | NG | NG | NG | NG |
| *Bacillus megaterium* ATCC 14581 | B | TGE | <3.9 | 125 | 46.9 | <17.6 |
| *Staphylococcus aureus* ATCC 6538 | B | TGE | 7.8 | 31.25 | 15.6 | 7.8 |

TABLE 4-continued (dodecylguanidine hydrochloride, $C_{12}$>98%)

| ORGANISM | TYPE | CULTURE MEDIUM | MIC | 2 HR MBC | 4 HR MBC | 24 HR MBC |
|---|---|---|---|---|---|---|
| Bacteria Mix | B | TGE | 62.5 | 117.2 | 86 | 78.2 |
| *Saccharomyces cerevisiae* ATCC 4111 | Y | SMA | 31.25 | 31.25 | 31.25 | NG |
| Pink Yeast | Y | SMA | 7.8 | <3.9 | <3.9 | <3.9 |
| Yeast Mix | Y | SMA | 15.6 | 31.25 | 31.25 | 15.6 |
| *Aspergillus niger* ATCC 6275 | M | SMA | 31.25 | 31.25 | 31.25 | 15.6 |
| *Aureobasidium pullulans* ATCC 9348 | M | Malt | <3.9 | <3.9 | <5.8 | <3.9 |
| *Penicillium pinophilum* ATCC 9644 | M | SMA | <3.9 | 11.7 | 11.7 | <5.4 |
| Mold Mix | M | SMA/Malt | 11.7 | 46.9 | 15.6 | 19.5 |
| Yeast/Mold Mix | Y/M | SMA/Malt | 7.8 | 62.5 | 31.25 | 7.8 |

B = Bacteria
Y = Yeast
M = Mold
TGE = Tryptone Glucose Extract Agar
SMA = Sabouraud Maltose Agar
Malt = Malt Agar
NG = No Growth

TABLE 5

(antimicrobial composition of the instant invention per Example I)

| ORGANISM | TYPE | CULTURE MEDIUM | MIC | 2 HR MBC | 4 HR MBC | 24 HR MBC |
|---|---|---|---|---|---|---|
| *Pseudomonas aeruginosa* ATCC 10145 | B | TGE | 62.5* | 375 | 156.2 | 156.2 |
| *Klebsiella pneumoniae* ATCC 4352 | B | TGE | NG | NG | NG | NG |
| *Bacillus megaterium* ATCC 14581 | B | TGE | <3.9 | 62.5 | 31.25 | 7.8 |
| *Staphylococcus aureus* ATCC 6538 | B | TGE | 7.8 | 23.4 | 15.6 | 11.7 |
| Bacteria Mix | B | TGE | 62.5 | 101.6 | 86 | 109.4 |
| *Saccharomyces cerevisiae* ATCC 4111 | Y | SMA | 31.25 | 31.25 | 31.25 | NG |
| Pink Yeast | Y | SMA | <3.9 | <3.9 | <3.9 | <3.9 |
| Yeast Mix | Y | SMA | 15.6 | 31.25 | 23.4 | 15.6 |
| *Aspergillus niger* ATCC 6275 | M | SMA | 19.5 | 46.9 | 31.25 | 23.4 |
| *Aureobasidium pullulans* ATCC 9348 | M | Malt | <3.9 | <3.9 | <3.9 | <5.4 |
| *Penicillium pinophilum* ATCC 9644 | M | SMA | <3.9 | 15.6 | 7.8 | <3.9 |
| Mold Mix | M | SMA/Malt | <5.8 | 62.5 | 23.4 | 11.7 |
| Yeast/Mold Mix | M | SMA/Malt | 11.7 | 62.5 | 31.25 | <3.9 |

B = Bacteria
Y = Yeast
M = Mold
TGE = Tryptone Glucose Extract Agar
SMA = Sabouraud Mattose Agar
Malt = Malt Agar
NG = No Growth The bacteria mix was prepared by streaking the bacteria on a tryptone glucose extract agar plate and incubated at 37° C. for a 24 hour period. A sterile swab of bacteria was placed into approximately 40 mls of trypticase soy broth (TSB); enough bacteria was added to form a turbid suspension. The broth was cultured for 24 hours, again at 37° C. After the 24 hour period, about 10 mls of the bacteria/broth suspension was added to approximately 90 mls of double strength trypticase soy broth (2XTSB). This procedure was repeated for each of the bacteria strains listed in Tables 4 and 5. Approximately 20 mls of each of the four bacteria/2XTSB solutions was then transferred to a separate container to form the bacteria mix.

The yeast mix was prepared by streaking the yeast on sabouraud maltose agar (SMA) and incubating the agar plates for at least 48 hours at 30° C. A sterile swab of yeast was placed into approximately 40 mls of double strength sabouraud maltose broth (2XSMB) and incubated an additional 24 hours at 30° C.; enough yeast was added to form a turbid suspension. Ten mls of the yeast/2XSMB solution was added to 40 mls of 2XSMB. This procedure was repeated for each of the yeast strains listed in Tables 4 and 5. Approximately 20 mls of each of the yeast/2XSMB solutions was then transferred to a separate container to form the yeast mix.

The mold mix was prepared by streaking the mold on slants of SMA and incubating the slants for at least 48 hours at 30° C. Approximately 5 mls of 2XSMB was added to the slants to form a suspension with the mold. This suspension was then transferred to a sterile glass bead bottle containing a small amount of additional 2XSMB. The bottle was shaken to cause release of the spores. The culture was then filtered through angle hair into a small specimen bottle. This was repeated for all of the mold species listed in Tables 4 and 5. Approximately 20 mls of the filtered mold/2XSMA solution was then transferred to a separate container to form the mold mix.

To form the yeast/mold mix, the same procedures as outlined above were followed for each individual yeast and mold specie. Approximately 20 mls of each of the yeast/2XSMB and mold/2XSMB solutions was then transferred to a separate container to form the yeast/mold mix.

The pink yeast is an environmental isolate available from Calgon Corporation, Pittsburgh, Pa.

Table 5 illustrates the efficacy of the antimicrobial composition of the present invention, in that the antimicrobial composition of the present invention killed all of the microorganisms to which it was exposed at the concentrations listed. A comparison of Tables 4 and 5 indicates that the overall performance of the antimicrobial composition of the present invention is at least equal to that of the dodecylguanidine hydrochloride composition that is currently commercially available against the bacteria and fungi tested. Further, comparison of the data of Tables 4 and 5 indicate that the MIC of the antimicrobial composition of the present invention required to result in no growth of Pink Yeast, *Aspergillus niger* ATCC 6275 and mold mix was significantly less than that of the currently commercially available dodecylguanidine hydrochloride composition.

Thus, it will be appreciated by those skilled in the art that the antimicrobial composition of the present invention and the process for making the antimicrobial composition of the instant invention results in providing a significantly improved antimicrobial composition having improved storage stability and safety (i.e., flash point) properties over conventional biocides.

Whereas particular embodiments of the instant invention have been described for the purposes of illustration, it will be evident to those skilled in the art that numerous variations and details of the instant invention may be made without departing from the instant invention as defined in the appended claims.

What is claimed is:

1. A process of preparing an antimicrobial composition having a storage stability below about 5° C. comprising:

(a) mixing a technical grade alkyl amine wherein said alkyl group has a carbon chain length distribution from about eight to eighteen carbon atoms such that from about 40 to 60 weight % of the alkyl group has a twelve carbon chain, with a solvent in a reactor to form a mixture of said alkyl amine and said solvent;

(b) adding hydrochloric acid to said alkyl amine solvent mixture and allowing heat of neutralization to warm the reactor from about 22° C. to 95° C.;

(c) adding hydrogen cyanamide to said reactor at a rate sufficient for maintaining the temperature of said alkyl amine, solvent, hydrochloric acid and hydrogen cyanamide mixture from about 75° C. to 95° C.;

(d) maintaining the temperature of said mixture of step (c) from about 75° C. to 95° C. for about four hours;

(e) cooling the mixture of step (d) to below about 30° C.;

(f) adding a sufficient amount of said solvent to dilute said mixture of step (e); and (g) adjusting the pH of said mixture of step (f) to less than 1.0.

2. The process of claim 1 including after step (e) adding a sufficient amount of water to dilute said mixture of step (e).

3. The process of claim 1 wherein said technical grade alkyl amine is a distilled coco amine.

4. The process of claim 1 wherein said solvent is selected from the group consisting of an alcohol having a carbon chain length of at least 3 carbon atoms and a glycol.

5. The process of claim 4 wherein said solvent is isopropyl alcohol.

6. The process of claim 4 wherein said solvent is dipropylene glycol.

* * * * *